(12) United States Patent
Fang et al.

(10) Patent No.: US 12,397,319 B2
(45) Date of Patent: Aug. 26, 2025

(54) EVENLY HEATING TRANSDUCER AND PREPARATION METHOD THEREFOR

(71) Applicant: Shanghai Hantong Medical Technology Co., Ltd., Shanghai (CN)

(72) Inventors: Yi Fang, Shanghai (CN); Bo Zhang, Shanghai (CN); Yong Wu, Shanghai (CN); Gang Peng, Shanghai (CN); Wanjin Zhao, Shanghai (CN)

(73) Assignee: Shanghai Hantong Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 19/023,520

(22) Filed: Jan. 16, 2025

(65) Prior Publication Data

US 2025/0187037 A1   Jun. 12, 2025

Related U.S. Application Data

(63) Continuation of application No. PCT/CN2024/121087, filed on Sep. 25, 2024.

(30) Foreign Application Priority Data

Dec. 12, 2023   (CN) .......................... 202311697482.6

(51) Int. Cl.
| | | |
|---|---|---|
| *H03H 9/13* | (2006.01) | |
| *A61N 7/02* | (2006.01) | |
| *B06B 1/06* | (2006.01) | |
| *H10N 30/045* | (2023.01) | |
| *H10N 30/072* | (2023.01) | |
| *H10N 30/88* | (2023.01) | |
| *A61N 7/00* | (2006.01) | |

(52) U.S. Cl.
CPC .............. *B06B 1/0651* (2013.01); *A61N 7/02* (2013.01); *H10N 30/045* (2023.02); *H10N 30/072* (2023.02); *H10N 30/88* (2023.02); *A61N 2007/003* (2013.01); *B06B 2201/76* (2013.01)

(58) Field of Classification Search
CPC .............................. B06B 1/0651; H10N 30/88
See application file for complete search history.

(56) References Cited

U.S. PATENT DOCUMENTS

| | | | | |
|---|---|---|---|---|
| 2009/0230822 | A1* | 9/2009 | Kushculey | B06B 1/0637 310/366 |
| 2012/0029358 | A1* | 2/2012 | Lin | A61B 8/0825 600/447 |
| 2013/0213628 | A1* | 8/2013 | Litovsky | H04R 1/2834 165/185 |
| 2017/0063327 | A1* | 3/2017 | Myjak | B06B 1/0253 |

FOREIGN PATENT DOCUMENTS

| | | |
|---|---|---|
| CN | 111063790 A | 4/2020 |
| CN | 116441149 A | 7/2023 |

* cited by examiner

*Primary Examiner* — Bryan P Gordon
(74) *Attorney, Agent, or Firm* — Jose Cherson Weissbrot

(57) ABSTRACT

The present application discloses an evenly heating transducer and a preparation method therefor. The transducer includes a piezoelectric material layer; where the piezoelectric material layer is cylindrical and has a through hole in the middle, a support structure is disposed on an inner side of the through hole, and the piezoelectric material layer and an external device are connected via the support structure. A conductive layer is disposed on a surface of the piezoelectric material layer and an isolation strip is disposed on the conductive layer.

9 Claims, 11 Drawing Sheets

EVENLY HEATING TRANSDUCER AND PREPARATION METHOD THEREFOR

CROSS-REFERENCE TO RELATED APPLICATIONS

The present application is a continuation of International Application No. PCT/CN2024/121087, with an international filing date of Sep. 25, 2024, which is based upon and claims priority to Chinese Patent Application No. 202311697482.6, filed on Dec. 12, 2023, the entire contents of all of which are incorporated herein by reference.

TECHNOLOGY FIELD

The present application relates to the technical field of medical devices, particularly to an evenly heating transducer and a preparation method therefor.

BACKGROUND

Hypertension is a common clinical disease. Renal artery ultrasound ablation is an ablation system based on a piezoelectric effect. An ultrasound transducer, when excited by a matching frequency signal, produces vibrations based on the piezoelectric effect and emits a 360° ultrasound wave field radially, where ultrasound waves are absorbed by external tissue to heat up, achieving 360° ablation.

Clinically, the existing ultrasound transducer is typically subjected to direct wire welding, resulting in thick welding points at the tail end of the ultrasound transducer. This is likely to cause uneven heating of the transducer during operation of the ultrasound transducer. Additionally, the design of ordinary electrodes means that about 20-30% of the overall region of the transducer in the axial direction is unable to undergo the piezoelectric effect, resulting in insufficient ablation length and low ablation efficiency. It is necessary to adjust the delivery position of the ultrasound transducer multiple times, causing repeated or prolonged ablation on portions without lesions or already ablated parts, increasing the clinical risk of patients.

SUMMARY

An object of the present application is to address the shortcomings in the prior art by providing an evenly heating transducer and a preparation method therefor.

To achieve the above objective, the present application adopts the following technical solution: An evenly heating transducer is provided, including:
  a piezoelectric material layer; wherein
  the piezoelectric material layer is cylindrical and has a through hole in the middle, a support structure is disposed on an inner side of the through hole, and the piezoelectric material layer and an external device are connected via the support structure; and
  a conductive layer is disposed on two sides of the piezoelectric material layer, an isolation strip is disposed on the piezoelectric material layer, the isolation strip divides the conductive layer into a positive electrode part and a negative electrode part, and after powered, the transducer produces even vibrations and radially emits sound waves that are afterwards absorbed by human tissue to heat up, achieving even heating.

As a further description of the foregoing technical solution, the support structure is a support column.

An evenly heating transducer is further provided, including:
  a piezoelectric material layer; wherein
  the piezoelectric material layer is cylindrical and has a through hole in the middle; and
  a conductive layer is disposed on two sides of the piezoelectric material layer, an isolation strip is disposed on the piezoelectric material layer, the isolation strip divides the conductive layer into a positive electrode part and a negative electrode part, and after powered, the transducer produces even vibrations and radially emits sound waves that are afterwards absorbed by human tissue to heat up, achieving even heating.

As a further description of the foregoing technical solution, the positive electrode part is located on an outer diameter surface of the piezoelectric material layer, and the negative electrode part is located on an inner diameter surface of the piezoelectric material layer, so as to form a first structure or a second structure.

As a further description of the foregoing technical solution, the first structure indicates the negative electrode part is located on the inner diameter surface of the piezoelectric material layer and does not exceed an end face of the piezoelectric material layer.

The second structure indicates the negative electrode part is located on the inner diameter surface of the piezoelectric material layer and a side end face of the piezoelectric material layer and extends towards the outer diameter surface.

As a further description of the foregoing technical solution, a ratio of a thickness to a diameter of the piezoelectric material layer is 2-10, and the thickness of the piezoelectric material layer is 0.5-1.5 mm.

As a further description of the foregoing technical solution, a thickness of the conductive layer is 10 μm-200 μm.

As a further description of the foregoing technical solution, the support structure is a spiral support structure or a C-shaped support structure.

As a further description of the foregoing technical solution, in a first structural state, the support structure is a spiral support structure;

As a further description of the foregoing technical solution, in a second structural state, the support structure is a C-shaped support structure with an opening size that is not more than ⅙ of a circumference.

As a further description of the foregoing technical solution, when the transducer has the first structure, the support structure has an outer diameter slightly greater than an inner diameter of the piezoelectric material layer, is in interference fitting with an inner wall of the piezoelectric material layer and elastically clamped on an inner side of the piezoelectric material layer, and has a radial overlap part with the piezoelectric material layer with a length not exceeding 1/10 of a total length of the piezoelectric material layer.

As a further description of the foregoing technical solution, part of the support structure located on an outer side of the piezoelectric material layer is welded to a wire and serves as a first stage of the transducer.

As a further description of the foregoing technical solution, a welding point position is located at 180° from an opening position of the C-shaped support structure.

A preparation method for transducer is further provided, where the preparation method is suitable for the transducer according to any one of the foregoing technical solutions, and includes the following steps:
  S1: performing electric field polarization, gas polarization, or thermal polarization, and sintering to form a piezoelectric material layer, and pre-treating an outer side of the piezoelectric material layer to improve surface adhesion;

S2: applying a polymer layer, adhesive glue, or wrapping tape to an inner side of an isolation strip;

S3: performing deposition on the outer side of the piezoelectric material layer through PVD or CVD to form a conductive layer, removing the conductive layer at a position of the isolation strip after formation of the conductive layer, and arranging the isolation strip on the piezoelectric material layer, such that the isolation strip divides the conductive layer on the outer side of the piezoelectric material layer into a positive electrode part and a negative electrode part; and S4: mounting a support structure on an inner side of the piezoelectric material layer and enabling connection to an external device via the support structure.

As a further description of the foregoing technical solution, the piezoelectric material layer is made of ceramic or polymer composite wafer.

As a further description of the foregoing technical solution, the positive electrode part and the negative electrode part of the conductive layer are made of a same material.

As a further description of the foregoing technical solution, the support structure is made of nickel-titanium, stainless steel, or titanium alloy.

The above technical solutions have the following advantages or beneficial effects:

Through the connection to an external device via the support structure, the difficulty that wires in the transducer cavity cannot be welded is resolved. The entire transducer can undergo the piezoelectric effect in the axial direction, allowing for a good heating length and annular heating effect. An excitation signal completely flows through the entire piezoelectric material layer, generating more even energy and ensuring a better ablation effect. This allows for 360° simultaneous ablation within the blood vessel, with a low processing difficulty and low production costs.

Figure 1:
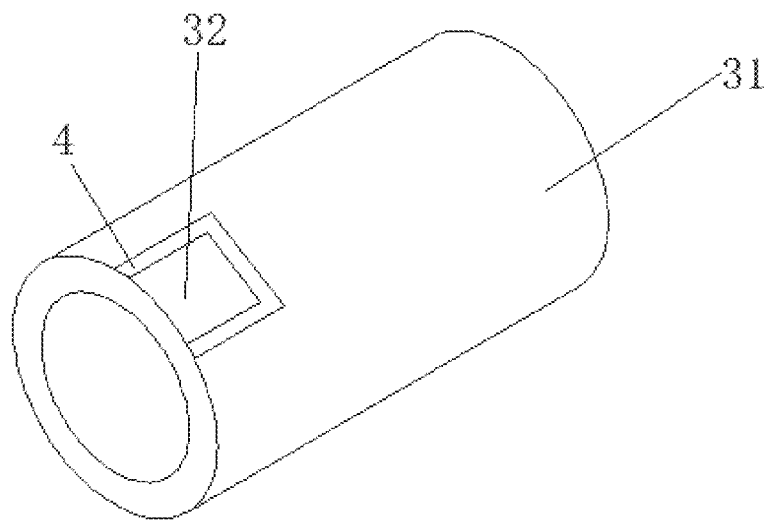
FIG. 1 is a first schematic structural diagram of a transducer according to the present application.
Figure 2:
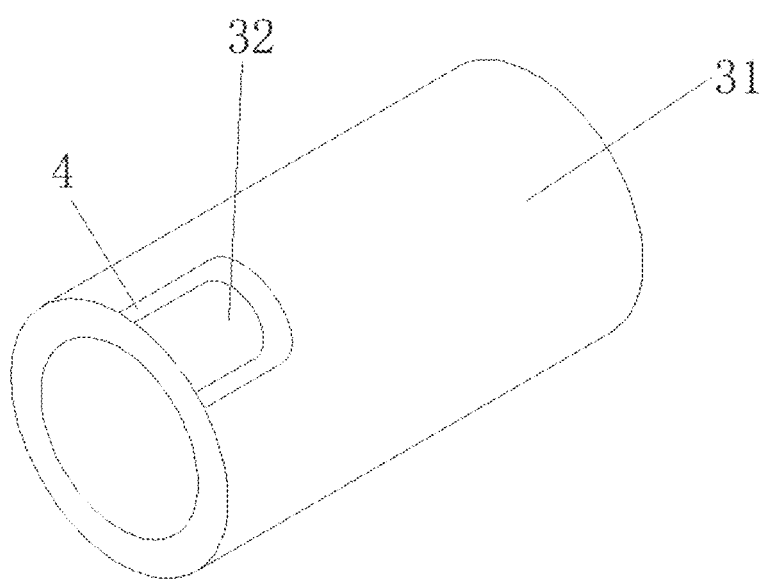
FIG. 2 is a second schematic structural diagram of the transducer according to the present application.
Figure 3:
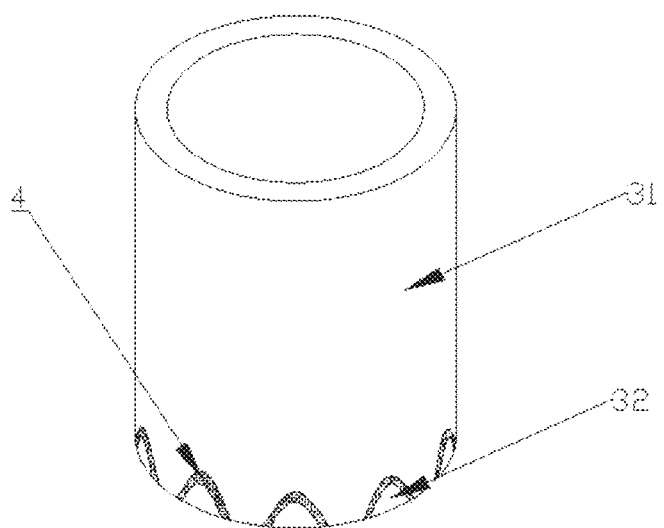
FIG. 3 is a schematic diagram of a wavy isolation strip of a first structure of the transducer according to the present application.
Figure 4:
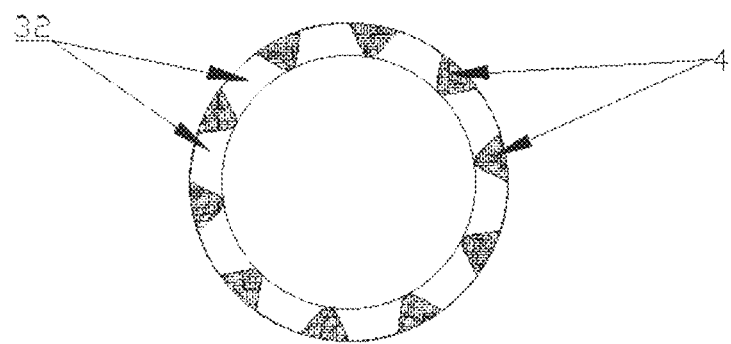
FIG. 4 is a schematic diagram of a sinusoidal isolation strip of the first structure of the transducer according to the present application.

DESCRIPTION OF REFERENCE NUMERALS 1. piezoelectric material layer; 2. support structure; 3. conductive layer; 31. positive electrode part; 32. negative electrode part; 4. isolation strip; 5. acoustic power of a structure in a circumferential direction, where an overlap size is ¹⁄₂₀ of a total length of the transducer; 6. acoustic power of a structure in a circumferential direction, where an overlap size is ⅕ of a total length of the transducer; 7. acoustic power of a structure in a circumferential direction, where the support structure 2 has an opening size being ¹⁄₁₀ of a circumference; 8. acoustic power of a structure in a circumferential direction, where an opening size is ⅕ of a circumference; and 9. external device.

DESCRIPTION OF THE EMBODIMENTS

The technical solutions of the embodiments of the present application are clearly described below with reference to the accompanying drawings of the embodiments of the present application. Apparently, the described embodiments are merely some rather than all of the embodiments of the present application. All other embodiments obtained by a person of ordinary skill in the art on the basis of the embodiments of the present application without creative efforts shall fall within the protection scope of the present application.

An embodiment of the present application provides an evenly heating transducer, including a piezoelectric material layer 1. The piezoelectric material layer 1 is cylindrical and provided with a through hole in the middle, a support structure 2 is disposed on an inner side of the through hole, and the piezoelectric material layer 1 is connected to an external device via the support structure 2. A conductive layer 3 is disposed on a surface of the piezoelectric material layer 1, and an isolation strip 4 is disposed on the conductive layer 3, the isolation strip 4 dividing the conductive layer 3 into a positive electrode part 31 and a negative electrode part 32. After powered, the transducer produces even vibrations and radially emits sound waves that are afterwards absorbed by human tissue to heat up, achieving even heating.

In this embodiment, the piezoelectric material layer 1 is cylindrical and provided with a through hole in the middle, and may further be arranged to be a tubular, square tubular, or oval-shaped structure as needed. The conductive layer 3 is prepared on both the inner and outer sides of the piezoelectric material layer 1. The piezoelectric material layer 1 is controlled to vibrate via the conductive layer 3, achieving electro-acoustic conversion. The support structure 2 is provided on the inner side of the piezoelectric material layer 1, such that it can be connected to an external device such as a polymer tube or a metal tube. This ensures the transducer is fixed while not restricting the radial direction of the transducer, especially the inward radial vibrations, thereby better achieving even heating of the transducer.

The isolation strip 4 is arranged on the outer side of the piezoelectric material layer 1 to divide the conductive layer 3 into the positive electrode part 31 and the negative electrode part 32, ensuring that the excitation signal transmitted through the wire completely flows through the conductive layer 3. The isolation strip 4 is typically made of a polymer material such as polytetrafluoroethylene or a ceramic material. Preferably, the isolation strip 4 can be formed by applying glue or a preset polymer layer in the conductive layer 3 on the piezoelectric material layer 1, preventing the conductive layer 3 from adhering to the isolation strip 4. In addition, the insulating property of the ceramic is used to isolate the positive and negative electrodes.

In this embodiment, the isolation strip 4 may be designed to be rectangular, semi-circular, or sinusoidal to suit different transducer structures.

The positive electrode part 31 is located on an outer diameter surface of the piezoelectric material layer 1, and the negative electrode part 32 is located on an inner diameter surface of the piezoelectric material layer 1, so as to form a first structure or a second structure.

In this embodiment, the conductive layer 3 is located on the outer surface of the piezoelectric material layer 1 and is divided by the isolation strip 4. The positive electrode part 31 and the negative electrode part 32 are connected to different wires. During the ablation operation, they are both connected to the input voltage, receiving excitation signals to control the piezoelectric material layer 1 to vibrate.

The first structure indicates that the negative electrode part 32 is located on the inner diameter surface of the piezoelectric material layer 1 and a side end face of the piezoelectric material layer 1 and extends towards the outer diameter surface.

The second structure indicates that the negative electrode part 32 is located on the inner diameter surface of the piezoelectric material layer 1 and does not exceed an end face of the piezoelectric material layer 1.

In this embodiment, the preparation of the negative electrode part 32 allows for two different structures of the transducer. When the negative electrode part 32 is located on the inner diameter surface of the piezoelectric material layer 1 and the positive electrode part 31 is located on the outer diameter surface of the piezoelectric material layer 1, there is no contact between the positive electrode part 31 and the negative electrode part 32, and both side end faces of the piezoelectric material layer 1 are arranged with no conductive layer 3 and are isolated due to the material property of the piezoelectric material layer 1 itself.

Figure 5:
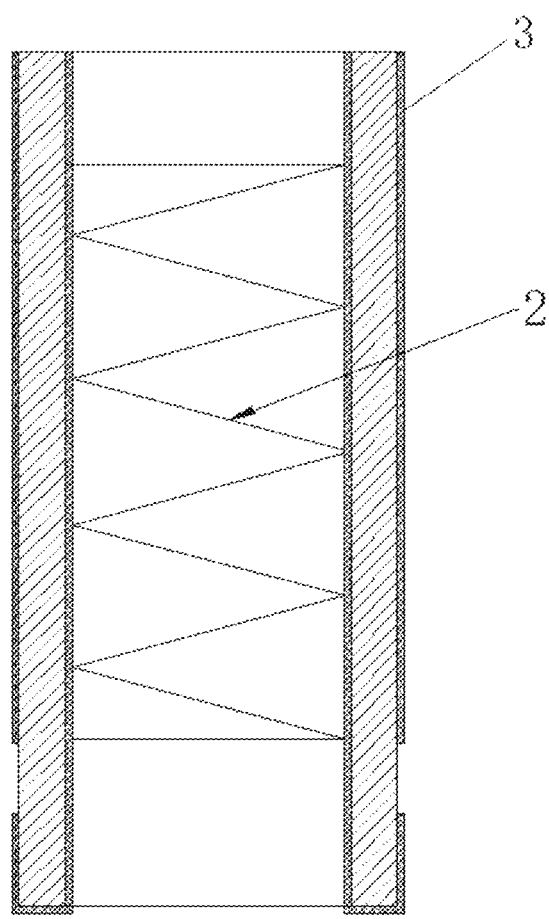
FIG. 5 is a schematic diagram of a support structure of the first structure of the transducer according to the present application.
Figure 6:
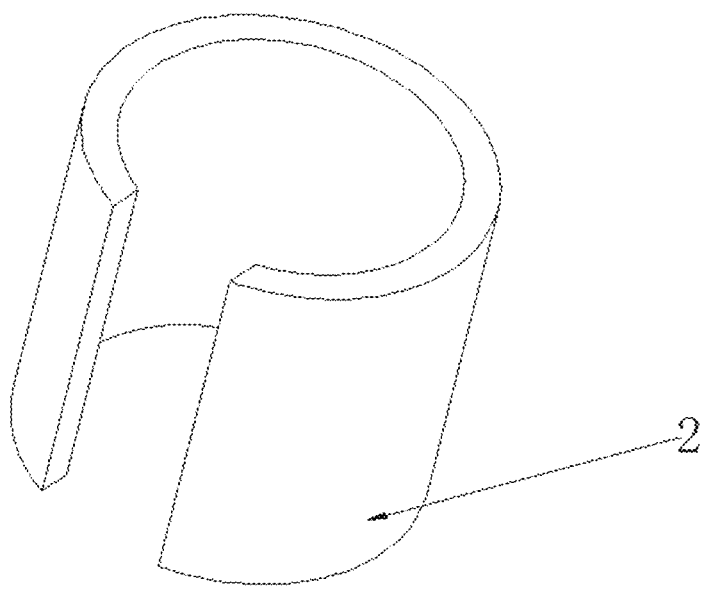
FIG. 6 is a schematic diagram of a C-shaped support column of a second structure of the transducer according to the present application.

Referring to FIG. 5, when part of the negative electrode part 32 extends through the cylindrical bottom surface of the piezoelectric material layer 1 to the outer diameter surface, for the connection of the negative electrode part 32 and the wire, the isolation strip 4 can be arranged to isolate the positive electrode part 31 from the negative electrode part 32, forming the first structure of the transducer in this embodiment.

Figure 7:
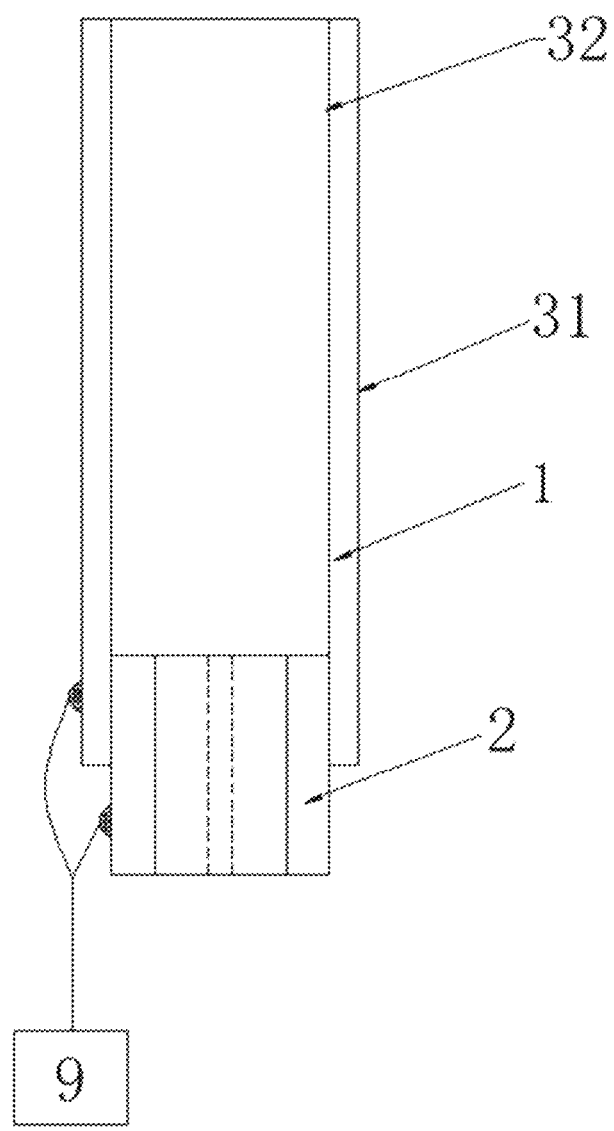
FIG. 7 is a schematic welding diagram of the C-shaped support column of the second structure of the transducer according to the present application.
Figure 8:
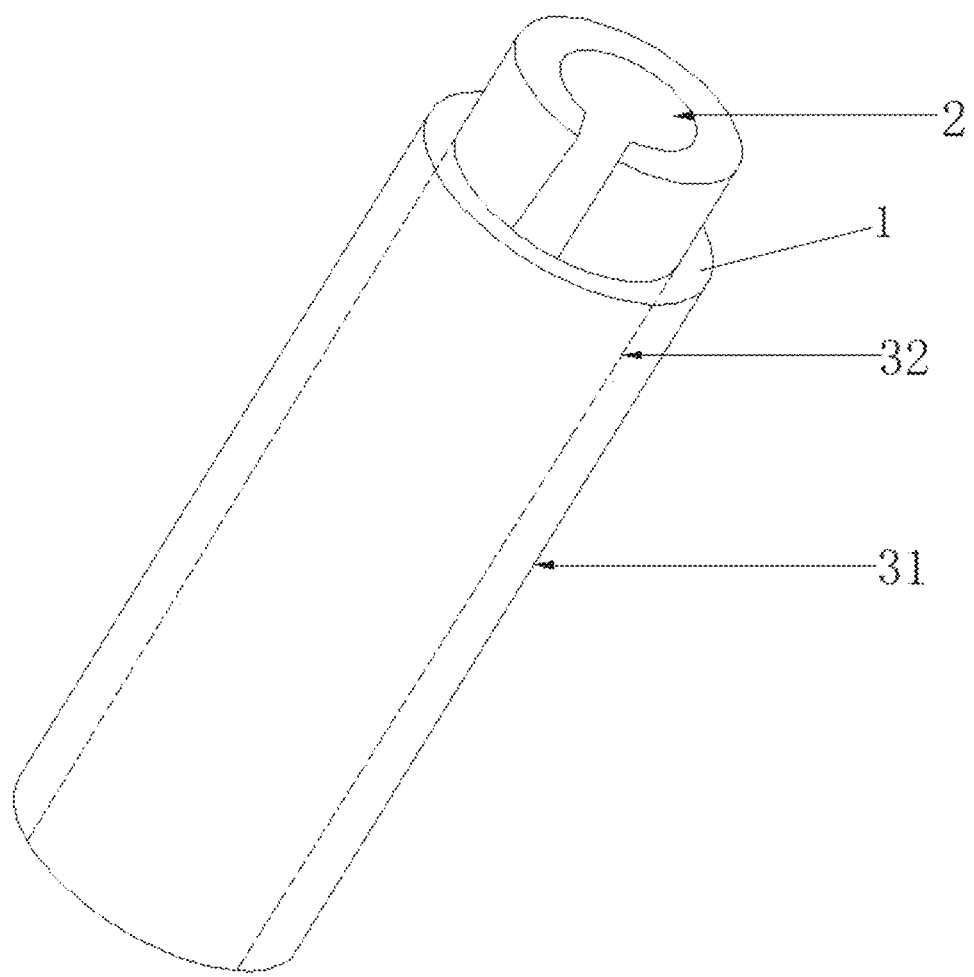
FIG. 8 is a three-dimensional diagram of the C-shaped support column of the second structure of the transducer according to the present application.

Referring to FIG. 7, the negative electrode part 32 is located on the inner diameter surface of the piezoelectric material layer 1 and does not exceed the end face of the piezoelectric material layer 1. The C-shaped support structure 2 is elastically clamped to the inner wall of the transducer, and the exposed part of the support structure is used to connect the wire and the negative electrode part of the transducer, forming the second structure of the transducer in this embodiment.

The support structure 2 is made of nickel-titanium, stainless steel, or titanium alloy.

In the embodiment of the first structure, the support structure 2 is made of nickel-titanium, which has better elasticity and less impact on the vibrations of the transducer, and is more conducive to the even heating of the transducer. The support structure 2 is preferably a spiral support column, providing internal support for the transducer and facilitating the fixing of the transducer. The wall of the spiral support column may be perforated to ensure support strength while reducing the weight of the support column, facilitating even heating of the transducer. The spiral support column may be perforated based on the needs of the transducer, reducing the contact area with the inside of the transducer and improving the heating efficiency of the transducer.

In the embodiment of the second structure, the support structure 2 is made of nickel-titanium, which has better elasticity and less impact on the vibrations of the transducer, and is more conducive to the even heating of the transducer. The outer diameter of the C-shaped support column of the support structure 2 is set to be slightly greater than the inner diameter of the negative electrode part 32 on the inner side of the piezoelectric material layer 1. Under external force, the outer diameter can be reduced, allowing the support structure 2 to be inserted into the through hole of the piezoelectric material layer 1. Based on its own elastic rebound, it is fixed to the inner wall of the piezoelectric material layer 1.

It is necessary to control the overlap size of the C-shaped support structure 2 with the inner wall of the transducer in the radial direction, and preferably, the overlap size is less than $1/10$ of the total length of the transducer.

Figure 9:
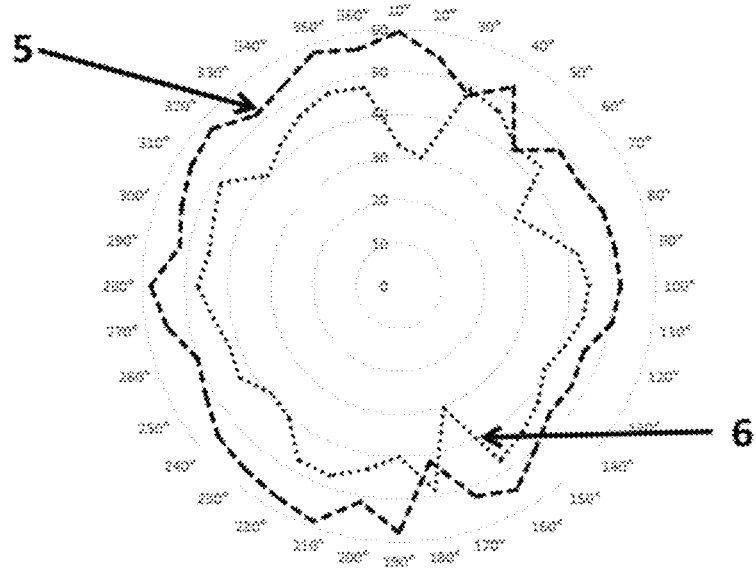
FIG. 9 is a schematic comparison diagram of acoustic powers of transducers with different overlap sizes in a circumferential direction according to the present application.

FIG. 9 shows a comparison of a sound power 5 of a structure with an overlap size being $1/20$ of the total length of the transducer in a circumferential direction and a sound power 6 of a structure with an overlap size being $1/5$ of the total length of the transducer in a circumferential direction. The sound power represents the heating condition of the transducer in the circumferential direction. The results show that a smaller overlap size can bring more uniform circumferential heating and higher sound power.

FIG. 7 shows the specific connection method of the C-shaped support structure 2 and the transducer, where the exposed part is directly welded to the wire, serving as the first stage of the transducer. The welding point is located at 180° from the opening position of the C-shaped support column, ensuring the heating evenness of the transducer. The other electrode is fixed to the outer diameter surface of the transducer using a conductive adhesive or through welding.

The opening size of the C-shaped support structure 2 needs to be less than $1/6$ of the circumference, that is, the opening angle is less than 30°, ensuring that the potential of the negative electrode part 32 of the conductive layer 3 is more even.

Figure 10:
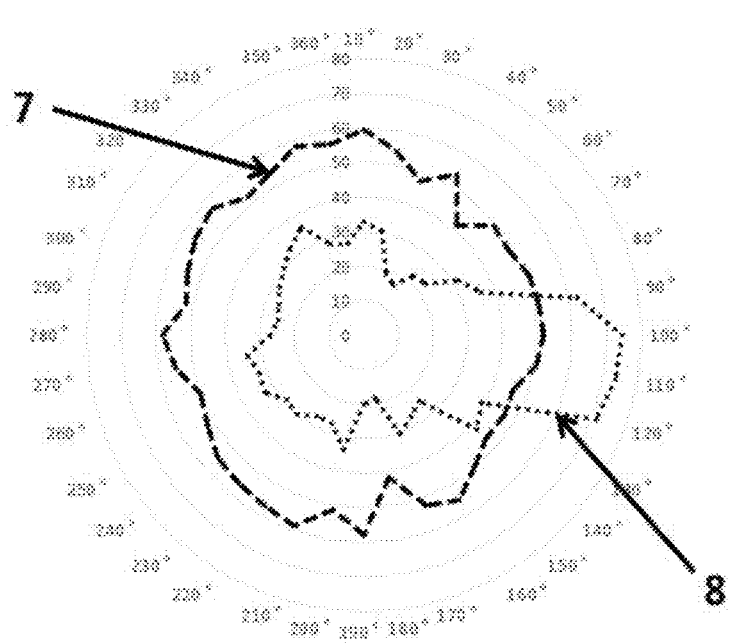
FIG. 10 is a schematic comparison diagram of acoustic powers of transducers having support structures with different opening sizes in a circumferential direction according to the present application.

FIG. 10 shows a comparison of a sound power 7 of a structure indicating an opening size of the support structure 2 is $1/10$ of the circumference in the circumferential direction and a sound power 8 of a structure indicating an opening size is $1/5$ of the circumference in the circumferential direction. The sound power represents the heating condition of the transducer in the circumferential direction. The results show that a smaller opening size of the support structure 2 can bring more even circumferential heating.

In all embodiments, a ratio of the thickness to the diameter of the piezoelectric material layer 1 is 2-10, and the thickness of the piezoelectric material layer 1 is 0.5-1.5 mm. In this embodiment, the thickness range of the piezoelectric material layer is 0.5-1.5 mm, and the diameter of the piezoelectric material layer is 1~4 mm. When the ratio of the diameter to the thickness is 3-6, the heating efficiency is higher.

The thickness of the conductive layer 3 is 10 µm-200 µm. In this embodiment, better conductivity is obtained without affecting the vibration effect of the piezoelectric material layer, thus improving energy conversion efficiency. Further, the thickness of the conductive layer 3 is 20 µm-50 µm, and a conductive material layer with such size allows for better conductivity. A too thick conductive material layer would affect the vibration effect of the piezoelectric material layer, reducing energy conversion efficiency.

The support structure 2 is a support column. In this embodiment, the support column is a spiral support column or a C-shaped support column, ensuring radial support and fixation while reducing the contact area with the inner side of the piezoelectric material layer 1. In addition, a more precise size design maintains the original resonance point of the transducer as much as possible, thereby better maintaining the optimal electro-acoustic conversion efficiency and other parameters of the transducer.

Figure 11:
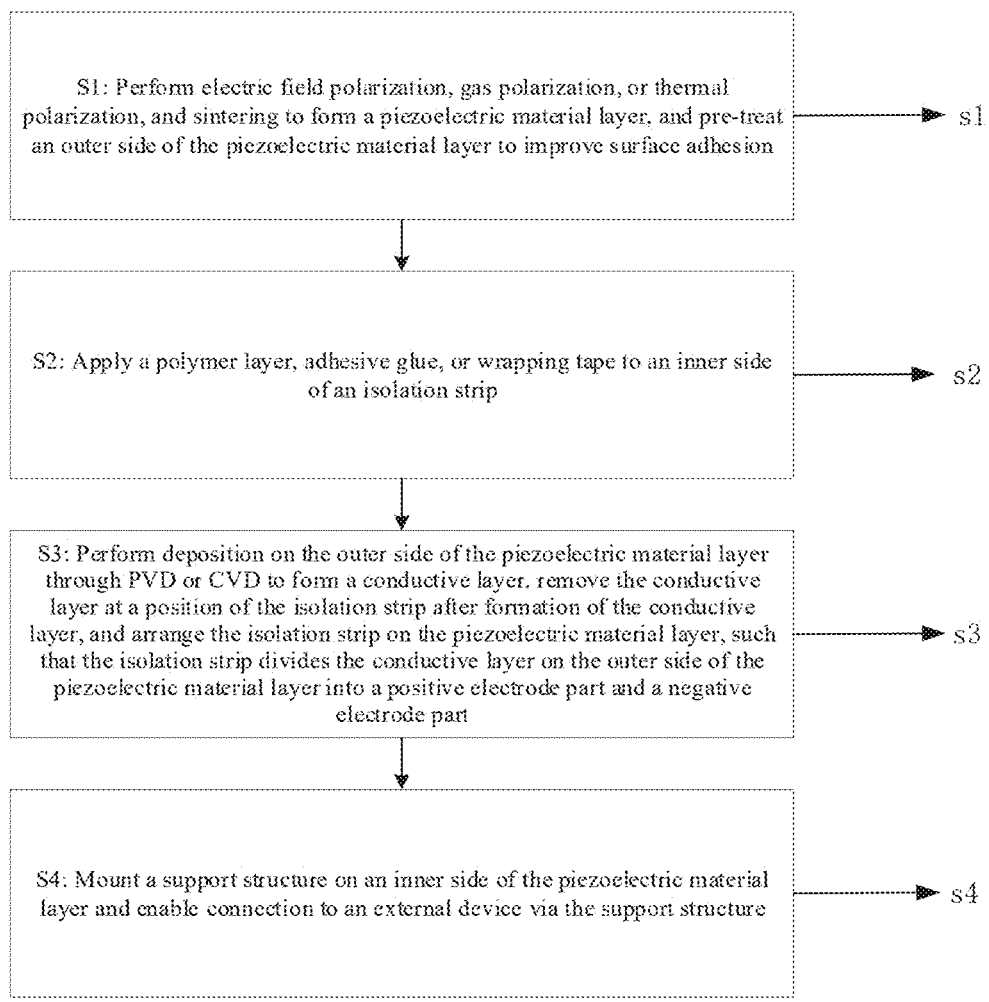
FIG. 11 is a flowchart of a preparation method for transducer according to the present application.

Referring to FIG. 11, an embodiment of the present application further provides a preparation method for transducer, where the preparation method is suitable for the transducer according to any one of the foregoing technical solutions, and includes the following steps:

S1: Perform electric field polarization, gas polarization, or thermal polarization, and sintering to form a piezoelectric material layer 1, and pre-treat an outer side of the piezoelectric material layer 1 to improve surface adhesion.

S2: Apply a polymer layer, adhesive glue, or wrapping tape to an inner side of an isolation strip 4.

S3: Perform deposition on the outer side of the piezoelectric material layer 1 through PVD or CVD to form a conductive layer 3, remove the conductive layer 3 at a position of the isolation strip 4 after formation of the conductive layer 3, arrange the isolation strip 4 on the piezoelectric material layer 1, such that the isolation strip 4 divides the conductive layer 3 on the outer side of the piezoelectric material layer 1 into a positive electrode part 31 and a negative electrode part 32.

S4: Mount a support structure 2 on an inner side of the piezoelectric material layer 1 and enable connection to an external device via the support structure 2.

In this embodiment, the piezoelectric material layer 1 is a hollow structure formed by polarizing and sintering ceramic/polymer composite wafer. After the piezoelectric material layer 1 is sintered, the surface is pre-treated using methods such as electrochemical, physical sandblasting, or plasma treatment to increase surface roughness, thereby enhancing the effect of being adhered to the conductive layer 3. Preferably, the plasma treatment is used to increase surface roughness and reduce damage to the piezoelectric material layer 1, preventing significant fluctuations in the resonance and anti-resonance frequency of the piezoelectric material layer 1. The plasma treatment can also enhance the adhesion and conductivity effects with the conductive layer 3.

After the pre-treatment is completed, the position of the isolation strip 4 is determined as needed. A polymer layer, adhesive glue, or wrapping tape is applied to the two end faces or the outer diameter of the piezoelectric material layer 1, so as to arrange the isolation strip 4. The conductive layer 3 is deposited on the outer side of the piezoelectric material layer 1 through PVD (physical vapor deposition) or CVD (chemical vapor deposition), preferably PVD (physical vapor deposition). After the deposition is completed, the portion provided with the isolation strip 4 protrudes upwards, and the excess conductive layer 3 is removed by etching, dividing the conductive layer 3 into the positive electrode part 31 and the negative electrode part 32, which are isolated by the isolation strip 4. The excitation signal can be completely transmitted to the piezoelectric material layer 1 via the conductive layer 3.

After the deposition of the conductive layer 3, the support structure 2 is disposed on the inner side of the piezoelectric material layer 1 to be in slight clearance fitting with the negative electrode part 32. Spot welding is performed between the support structure 2 and an external device 9, with the welding position at 180° from the opening position of the C-shaped support structure 2. Spot welding is also performed between the conductive layer 3 and the external device 9. Compared with the existing method of directly applying annular welding between the conductive layer 3 and the external device 9, this method allows for a smaller welding area and more even heating.

The piezoelectric material layer 1 is made of ceramic or polymer composite wafer.

In this embodiment, the piezoelectric material layer 1 is selectively made of an insulating material. During the preparation of the conductive layer 3, it prevents connection between the positive electrode part 31 and the negative electrode part 32.

The positive electrode part 31 and the negative electrode part 32 of the conductive layer 3 are made of the same material.

The conductive layer 3 is usually made of a metal material with good conductivity and strong oxidation resistance. In this embodiment, gold is preferred, which has good conductivity and oxidation resistance.

Finally, it should be noted that the above descriptions are only preferred embodiments of the present application and are not intended to limit the present application. Although the present application has been described in detail with reference to the aforementioned embodiments, those skilled in the art can still make modifications to the technical solutions described in the aforementioned embodiments or make equivalent replacements for some technical features. Any modifications, equivalent replacements, or improvements made within the spirit and principles of the present application should be included in the protection scope of the present application.

What is claimed is:

1. An evenly heating transducer, comprising:
a piezoelectric material layer; wherein
the piezoelectric material layer is cylindrical and has a through hole in the middle, a support structure is disposed on an inner side of the through hole, and the piezoelectric material layer and an external device are connected via the support structure;
a conductive layer is disposed on two sides of the piezoelectric material layer, an isolation strip is disposed on the piezoelectric material layer, the isolation strip divides the conductive layer into a positive electrode part and a negative electrode part, and after powered, the transducer produces even vibrations and radially emits sound waves that are afterwards absorbed by human tissue to heat up, achieving even heating;
the support structure is a support column;
the support structure is a spiral support structure or a C-shaped support structure; and
the positive electrode part is located on an outer diameter surface of the piezoelectric material layer, and the negative electrode part is located on an inner diameter surface of the piezoelectric material layer to enable a first structural state or a second structural state; wherein the first structural state is where the negative electrode part is located on the inner diameter surface of the piezoelectric material layer and does not exceed an end face of the piezoelectric material layer;

in the first structural state, the support structure is a spiral support structure;

the second structural state is where the negative electrode part is located on the inner diameter surface of the piezoelectric material layer and a side end face of the piezoelectric material layer and extends towards the outer diameter surface;

in the second structural state, the support structure is a C-shaped support structure with an opening size that is not more than ⅙ of a circumference; and when the transducer is in the first structural state, the support structure has an outer diameter slightly greater than an inner diameter of the piezoelectric material layer, is in interference fitting with an inner wall of the piezoelectric material layer and elastically clamped on an inner side of the piezoelectric material layer, and has a radial overlap part with the piezoelectric material layer with a length not exceeding ⅒ of a total length of the piezoelectric material layer.

2. The transducer according to claim 1, wherein a ratio of a thickness to a diameter of the piezoelectric material layer is 2-10, and the piezoelectric material layer has a thickness of 0.5 to 1.5 mm.

3. The transducer according to claim 1, wherein the conductive layer has a thickness of 10 μm to 200 μm.

4. The transducer according to claim 1, wherein part of the support structure located on an outer side of the piezoelectric material layer is welded to a wire and serves as a first stage of the transducer.

5. The transducer according to claim 1, wherein a welding point position is located at 180° from an opening position of the C-shaped support structure.

6. A preparation method for the transducer of claim 1, comprising the following steps:
   S1: performing electric field polarization, gas polarization, or thermal polarization, and sintering to form a piezoelectric material layer, and pre-treating an outer side of the piezoelectric material layer to improve surface adhesion;
   S2: applying a polymer layer, adhesive glue, or wrapping tape to an inner side of an isolation strip;
   S3: performing deposition on the outer side of the piezoelectric material layer through PVD or CVD to form a conductive layer, removing the conductive layer at a position of the isolation strip after formation of the conductive layer, and arranging the isolation strip on the piezoelectric material layer, such that the isolation strip divides the conductive layer on the outer side of the piezoelectric material layer into a positive electrode part and a negative electrode part; and
   S4: mounting a support structure on an inner side of the piezoelectric material layer and enabling connection to an external device via the support structure.

7. The preparation method according to claim 6, wherein the piezoelectric material layer is made of ceramic or polymer composite wafer.

8. The preparation method according to claim 6, wherein the positive electrode part and the negative electrode part of the conductive layer are made of a same material.

9. The preparation method according to claim 6, wherein the support structure is made of nickel-titanium, stainless steel, or titanium alloy.

* * * * *